United States Patent [19]

McManigill

[11] 4,003,679
[45] Jan. 18, 1977

[54] HIGH PRESSURE PUMP WITH METERING
[75] Inventor: Douglass McManigill, Menlo Park, Calif.
[73] Assignee: Hewlett-Packard Company, Palo Alto, Calif.
[22] Filed: Apr. 2, 1975
[21] Appl. No.: 564,246
[52] U.S. Cl. .............................. 417/246; 417/248; 417/385; 417/388
[51] Int. Cl.² ...................... F04B 3/00; F04B 9/08
[58] Field of Search .......... 417/246, 248, 265, 385, 417/388, 244

[56] References Cited
UNITED STATES PATENTS

| 1,650,377 | 11/1927 | Nixon | 417/388 |
| 3,232,524 | 2/1966 | Rice et al. | 417/248 |
| 3,433,161 | 3/1969 | Vetter | 417/388 |

FOREIGN PATENTS OR APPLICATIONS

| 305,235 | 2/1929 | United Kingdom | 417/383 |

Primary Examiner—William L. Freeh
Assistant Examiner—G. P. LaPointe
Attorney, Agent, or Firm—Ronald E. Grubman

[57] ABSTRACT

A pumping system is provided in which a low pressure metering pump injects fluid charges into a high pressure pump which in turn operates into a high pressure load. The high pressure pump is designed to always present a low pressure at its input on its intake stroke. This insures that the metering pump will always operate into a low pressure regardless of the load, and will therefore be enabled to always accurately meter charges into the high pressure pump.

In various embodiments, the high pressure pump and/or the low pressure pump include spring elements for providing well defined pumping pressures.

In some embodiments, an oil reservoir and diaphragm provide a well defined pressure against which the metering pump can operate.

11 Claims, 3 Drawing Figures

HIGH PRESSURE PUMP WITH METERING

BACKGROUND OF THE INVENTION

For many applications, and particularly for the practice of high pressure liquid chromatography, there is required a fluid pumping system which can accurately and reproducibly pump metered amounts of fluids into a high pressure load. It is important that the fluid flow be precisely controlled independently of the pressure of the load. Particularly if a chromatography system is to utilize gradient elution in which different fluids are to be mixed, the amount of each fluid must be precisely measurable at any given load pressure.

In the prior art, there are known different fluid delivery systems for liquid chromatography. It has been a problem with the prior art devices that the compressibility of the fluid and the mechanical compliance of the pump combine to cause a severe drop in flow rate as the load pressure increases, this phenomenon being commonly referred to as "roll off." To accurately meter the fluid flow, some presently known delivery systems employ a flow transducer which generates electrical feedback to control the pumping rate of the mechanical pump. However, these sensors typically depend on a measurement of differential pressure drop across a flow restrictor. Since the pressure drop depends on liquid viscosity which is a function of temperature, the flow sensor must be precisely maintained at a constant temperature; this is inconvenient and expensive. Furthermore, if a small particle or other residue lodges in the restricted area, a change in pressure reading results. Additionally, recalibration of flow sensors is necessary when a different fluid is being pumped.

SUMMARY OF THE INVENTION

In accordance with the illustrated preferred embodiments, the present invention provides a pumping system which can accurately and reproducibly control flow rate as a fluid is pumped into varying pressure loads up to very high pressures. No flow sensors are required. The device is particularly well suited for use in liquid chromatography systems, and in some embodiments may be used in gradient elution type systems. A low pressure metering pump is utilized to accurately meter charges of fluid and inject these metered charges into a high pressure pump on the intake stroke of this latter pump. The high pressure pump is designed to deliver to a high pressure load whatever solvent charge is introduced at its intake. In accordance with the invention, the high pressure pump is constructed so that on its intake stroke a low pressure is always presented to the low pressure metering pump. The metering pump, therefore, always operates into a low pressure regardless of the high pressure of the ultimate load, and is thereby enabled to accurately meter fluid charges independent of the load pressure.

In accordance with certain embodiments, the high pressure pump includes a tensioning spring to provide the desired low pressure seen by the metering pump. In other embodiments, the metering pump works against a diaphragm in the high pressure pump which is tensioned by oil from an oil reservoir. The low pressure pump therefore effectively pumps against the pressure required to deform the diaphragm into a cavity containing the oil; again the metering pump is enabled to always operate into a low pressure to insure accurate metering.

In various embodiments, the invention also provides for spring tensioning of a piston in the low pressure metering pump in such a way that the amount of liquid charge passed therethrough is accurately determined by a fixed displacement of the piston.

DETAILED DESCRIPTION OF THE INVENTION

Figure 1:
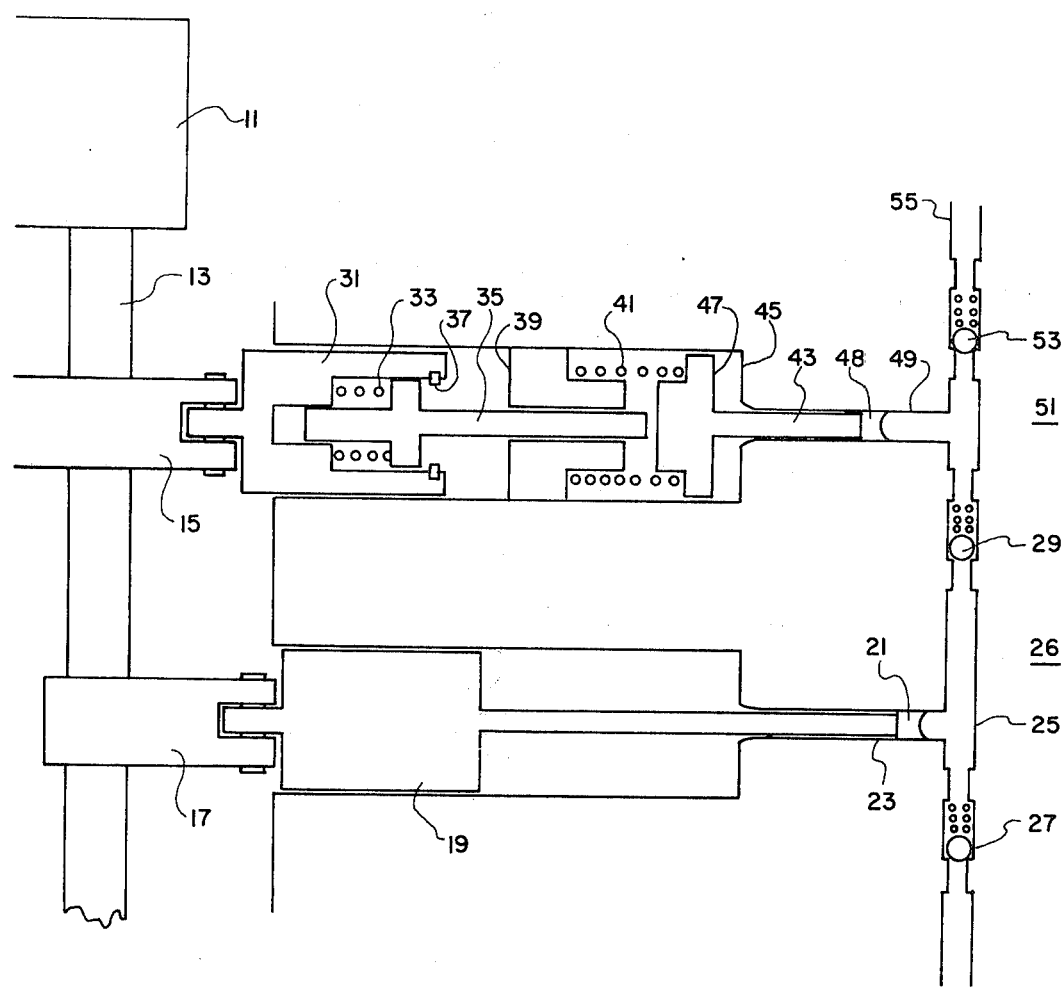
FIG. 1 illustrates a pumping system according to a preferred embodiment of the invention.

In FIG. 1 there is schematically illustrated a low pressure metering pump 26 which injects measured amounts of liquid into a high pressure pump 51. The pumping action of pump 26 is initiated by a variable speed motor 11 which drives a shaft 13. A Pittman arm 17 is connected to and driven by shaft 13. Pittman arm 17 in turn drives a piston assembly 19 including a tightly sealed piston tip 21 which effectively seals a cylinder-like portion 23 of the pump 26. Piston tip 21, cylinder 23, and another cylinderical cavity 25 define a portion of pump 26. To complete the low pressure pump assembly, there are included an entrance valve 27 and an exit valve 29. Fluid flow through this low pressure pump will be proportional to a very high precision to the speed of motor 11, provided the back pressure seen at exit valve 29 is relatively low, e.g., less than a pressure of 100 psi.

Turning now to a second pump and related assembly, a Pittman arm 15 drives a carrier 31 which carries a spring 33 and an anvil 35. A snap ring 37 retains anvil 35 against spring 33 so that the spring is compressed and exerts a force against the anvil. By way of reference, this force will hereafter be designated as F33. A stationary guide element 39 serves to center anvil 35, and also to position a second spring 41 so that this latter spring exerts a force to the right against another piston 43. This latter force will hereafter be designated F41. This force drives piston 43 to the right until its motion is limited by a stop surface 45 which contacts a shoulder 47 of the piston. Piston 43 terminates in a piston tip 48 which forms a high pressure seal in a cylindrical enclosure 49. High pressure pump 51 also includes an entrance valve 29 and an exit valve 53. In the embodiment illustrated here, the entrance valve 29 to pump 51 functions also as the exit valve for pump 26, but separate valves may be employed.

In operation, Pittman arm 15 forces anvil 35 into contact with piston 43 once for each rotation of crank 13. Piston 43 is therefore driven to the right until surface 47 contacts stop surface 45. The Pittman arm then continues its travel to the right forcing a compression of spring 33. The spring force F33 thus acts to pump a charge of fluid in pump 51 out through exit valve 53, provided only that the pressure in an output tube 55 is less than the pressure determined by the force F33.

In accordance with the principles of the present invention, pump 26 operates as a metering pump for accurately metering a charge of fluid to be delivered into the main chamber of pump 51. The apparatus is therefore designed so that pump 26 will always deliver its charge into a low pressure resistance from pump 51. This is accomplished by adjusting the phase of Pittman arm 17 relative to Pittman arm 15 so that piston 19 of pump 26 does not move to the right until anvil 35 of pump 51 has moved back to the left and is no longer in contact with piston 43. Thus when pump 26 commences to pump its charge into pump 51 through valve 29, it delivers against a pressure determined only by spring 41. This pressure is approximately equal to F41 divided by the area of cylinder 49. By suitably selecting spring 41, the force F41 can be made sufficiently weak so that the pressure seen by pump 26 is always low enough that pump 26 can accurately meter a charge of fluid pumped into the chamber of pump 51.

After a charge of fluid is injected into the cavity of pump 51, pump 51 drives the fluid into output tube 55 under the influence of spring force F33. This force can be made very strong so that pump 51 is able to deliver this charge into a high pressure load. The invention therefore provides an overall pumping mechanism which on the one hand can pump into high pressure loads and on the other hand provides very accurate metering of the fluid flow.

It may now be seen that the problem of pressure roll off is substantially eliminated in a pump according to the present invention. This may be best demonstrated by means of an operating example. Thus, consider a case where a high pressure (e.g., 10,000 psi) exists in outlet tube 55. When motor 11 commences rotation, pump 26 will deliver an initial charge, say of volume $V_1$ into the chamber of pump 51. Pump 51 will drive the pressure of this charge up to 10,000 psi and then expel the charge out through exit valve 53 into tube 55, until piston 43 strikes stop surface 45. At this time, the volume of fluid in pump 51 (hereafter referred to as the "dead volume") is the volume contained between piston tip 48, valve 53, and valve 29. Referring to this volume as $V_{D51}$ it can be shown that when anvil 35 retracts and releases piston 43, volume $V_{D51}$ will expand to a volume $V_{51}$ given approximately by $V_{51} = V_{D51} *(10,000 \text{ psi}/\mu) + C \times 10,000 \text{ psi}$, where $\mu$ is the bulk modulus of the fluid being pumped and C is the overall compliance of the chamber. This excess volume does not flow back through valve 29, but instead pushes piston 43 back slightly against spring 41. Since the excess volume did not flow through output valve 53, the initial charge delivered to the 10,000 psi load was less than the metered charge $V_1$ by the amount of $V_{51}$. This is the so-called roll off phenomenon common to high pressure metering pumps. In the present invention, however, on the next forward stroke of piston 43, the volume of fluid in pump 51 will be a new volume which is the sum of $V_1$ received from metering pump 26, plus the expansion volume of $V_{51}$ already in the chamber. Since the excess volume of $V_{51}$ is precisely the expansion volume at 10,000 psi, it is clear that on the second and all subsequent strokes an amount of fluid precisely equal to the full metered charge $V_1$ will be delivered to the load. It is simple to show that in a practical liquid chromatograph the effect of the undersized initial charge is insignificant. Moreover, it is common practice to begin the chromatographic run with the pump already running and fully up to pressure so that the undersized initial charge would be completely eliminated from the analysis. Thus, a pump according to the present invention, will not suffer from the commonly encountered difficulty of roll off at high pressures.

Should it happen that no charge is delivered from pump 26 to pump 51 on a particular stroke, spring 41 will maintain pressure against piston 43 to keep the piston pressed forward against stop 45. The piston will therefore remain stationary during the intake stroke and the subsequent delivery stroke. Pump 51 is thereby prevented from creating a vacuum during its intake stroke and sucking a charge through pump 26. This assures that no spurious charges will enter pump 51.

Figure 2:
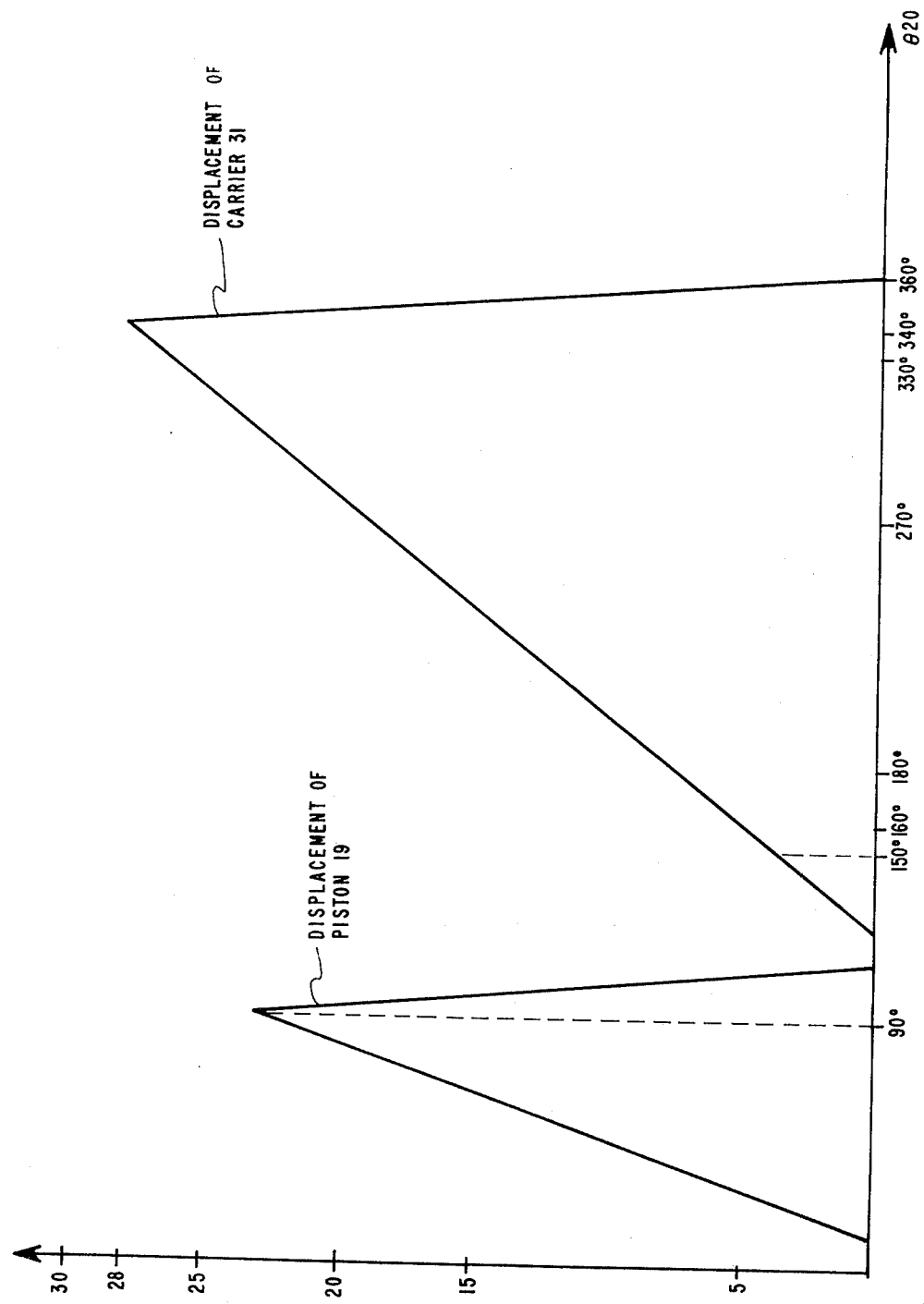
FIG. 2 is a diagram illustrating relative phases of the operating components of high pressure pump and metering pump during operation.

An alternate embodiment of the invention may be constructed by replacing each Pittman arm 15 and 17 by a cam assembly to drive carrier 31 and piston assembly 19 respectively. FIG. 2 is a diagram showing the position of carrier 31 and the position of piston assembly 19 as a function of the angular position of shaft 13, denoted by the angle $\theta$. In the particular example diagrammed piston tip 21 of pump 25 moves to the right a distance equal to 23 units when shaft 13 rotates between $\theta = 10°$ and $\theta = 90°$, thereby metering in a fixed volume $V_1$ to pump 51.

Suppose first that pump 51 is delivering into a low pressure in tube 55. There would thus be essentially zero expension volume in pump 51 prior to the introduction of the charge $V_1$. Under these conditions, anvil 35 would contact piston 43 when $\theta = 150°$. The volume $V_1$ would be linearly delivered to the load over the next 23 divisions of movement of carrier 31 (i.e., equivalent to 180° of $\theta$). The charge $V_1$ would therefore be fully delivered when $\theta$ was 330° and the displacement of carrier 31 was equal to 26.8 divisions. At this point, piston 47 strikes stop 45 and delivery ceases. Carrier 31, however, continues its forward motion until its displacement equals 28 divisions (when $\theta$ equals 340°), thereby compressing spring 41. Thereafter carrier 31 returns rapidly back to zero. displacement at $\theta = 360°$, and a new cycle begins.

Now, when pump 51 delivers into a high pressure, there will be an expansion volume $V_{51}$ from the previous cycle in the chamber of pump 51 to which the new charge $V_1$ must be added. Thus, anvil 35 will strike piston 43 at some $\theta < 150°$. It will be recalled from the above discussion that the expansion volume $V_{51}$ is precisely the volume by which the dead volume $V_{D51}$ must be compressed so that its pressure will be equal to the output pressure into 55. Thus, the movement of piston 43 will be precisely that required to deliver all of the charge $V_1$ to the load when piston 43 strikes stop 45. However, because pump 51 must now compress the total charge $V_1$, plus $V_{51}$ to the output pressure before flow can begin, the flow will not commence until $\theta$ equals some angle greater than 150°. This has the effect of preventing the realization of a uniform delivery rate; i.e., there will be some flow ripple at the pump output. This ripple is not to be confused with the roll off due to pump compliance and fluid compression which has been eliminated; that, is net delivery will be accurate regardless of output pressure, but there may still be some flow ripple. This ripple can be greatly reduced by including a second pumping system identical to the first pumping system but offset in phase of rotation by 180°.

Figure 3:
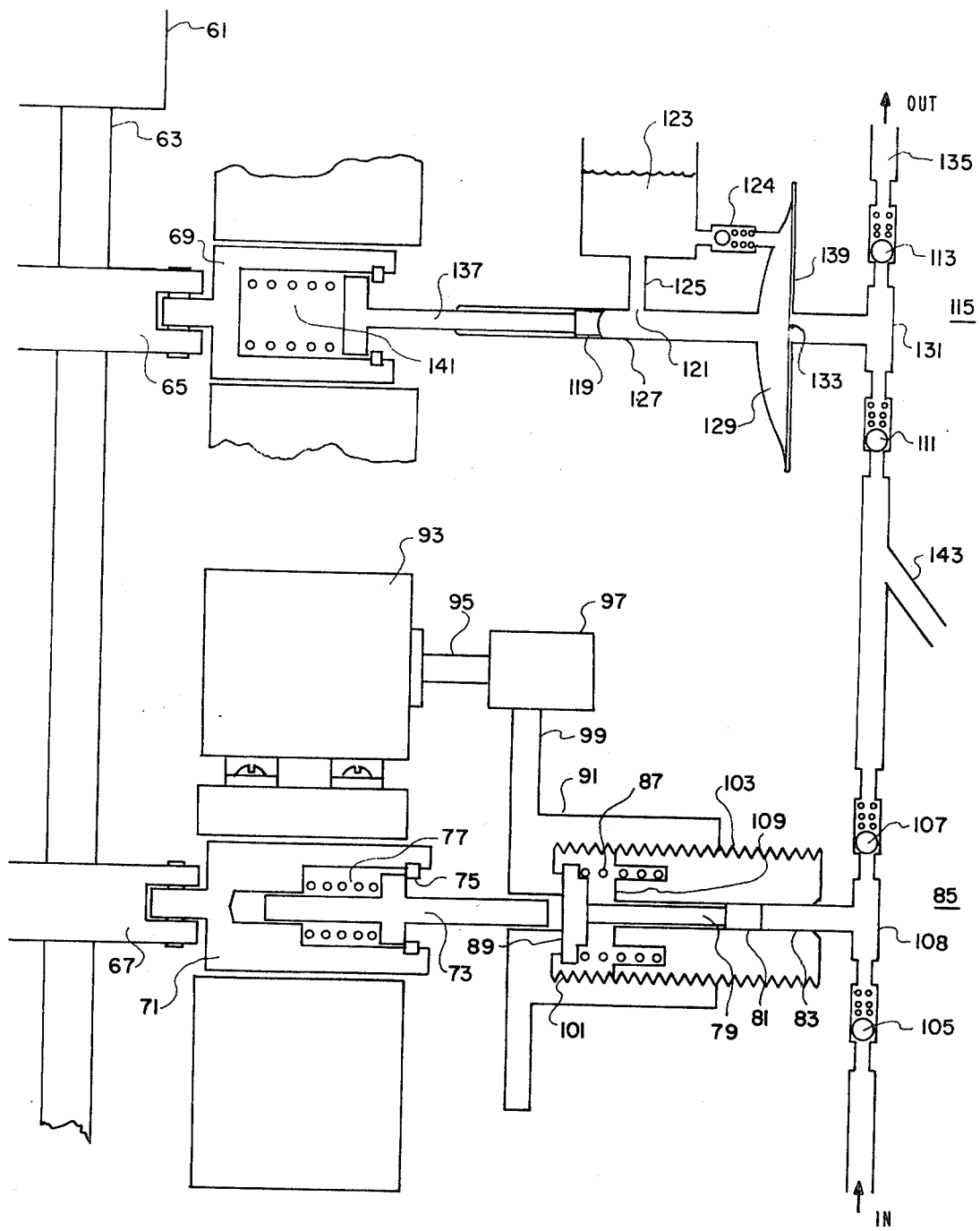
FIG. 3 shows another preferred embodiment of a pumping system.

In FIG. 3 there is illustrated another embodiment of the invention in which a low pressure metering pump 85 injects fluid charges into a pump 115. In this embodiment, a synchronous motor 61 drives a shaft 63 at a constant angular speed. A Pittman arm 65 connects the shaft to a drive carrier 69 and another Pittman arm 67 connects the same shaft to a second drive carrier 71. An anvil 73 is pressed forward against a snap ring 65 by the force exerted by a spring 77. A piston 79 includes a piston tip 81 to form a seal in a cylindrical-like portion 83 of pump 85. A spring 87 presses piston 79 back against a stop surface 89 which is a portion of a stop assembly 91. As will be described immediately below, stop assembly 91 is itself movable with respect to pump 85; the translational position of stop surface 89 is controlled by a stepping motor 93 which drives a shaft 95. This shaft induces rotation of a pinion 97 which engages a ring gear 99 on movable stop assembly 91. The entire assembly 91 thus rotates so that a set of threads 101 engages another set of threads 103 which are stationary with respect to pump 85. Rotation of stepping motor 93 therefore induces translational motion of movable assembly 91 to the right or to the left. Low pressure metering pump 85 includes an intake valve 105, a cavity portion including cylinder portions 83 and 108, piston tip 81 and exit valve 107.

In operation, metering pump 85 acts to expel liquid charges from exit valve 107. The volume of each charge (say $V_1$) depends only on the distance between stop surface 89 and a second stop surface 109 so that very accurate metering may be obtained. This is accomplished as follows: Pittman arm 67 drives carrier 71 until anvil 73 contacts piston 79 which is itself initially at rest against stop 89. As the Pittman arm continues its forward motion, carrier 73 drives piston 79 against stop 109. Pittman arm 67 is then driven even further forward in order to compress spring 77, which should be sufficiently stiff that its spring force is stronger than the sum of the spring force of spring 87 and the resistance of piston 79 to pumping motion. On the return stroke, anvil 73 is carried sufficiently far back to the left that piston 79 strikes stop 89, and contact between anvil 73 and the piston is broken. It is now evident that the charge $V_1$ which is expelled through exit valve 107 is determined solely by the distance between stops 89 and 109 and is therefore precisely determinable. By advancing or retarding stepping motor 93, the distance between stops may be adjusted, thereby determining the amount of charge to be metered by pump 85 into high pressure pump 115.

In this embodiment of the invention, high pressure pump 115 includes an intake valve 111 and an exit valve 113 which together with a diaphragm 133 delineate the boundaries of an enclosed cavity 131. A charge expelled from metering pump 85 will enter pump 115 through entrance valve 111. A piston 137 is driven by Pittman arm 65 whose phase is adjusted relative to the phase of Pittman arm 67 so that a piston tip 119 is always positioned to the left of an oil hole 121 when a charge is pumped into pump 115 from pump 85. Oil hole 121 connects a tube 125 leading from an oil reservoir 123 to a cylindrical chamber 127. This cylindrical chamber itself empties into a larger chamber 129 behind diaphragm 133. When piston tip 119 is to the left of oil hole 121, chambers 127 and 129 are filled with oil from the reservoir at atmospheric pressure. When a charge is pumped into pump 115 through valve 111, valve 113 is held closed by the high pressure existing in an output tube 135. Thus, as the charge is pumped into chamber 131, it is forced to deform diaphragm 133 to the left, the diaphragm therefore extending into chamber 129. The pressure seen by metering pump 85 is therefore that pressure required to deform diaphragm 133 when the charge enters pump 115. Diaphragm 133 should be sufficiently thin and of large enough diameter that this pressure is sufficiently low to ensure accurate metering by pump 85. In practice, diaphragms of thickness in the range 0.006 to 0.016 inch and a diameter of about 1.0 inch have been used with good results. After the charge from pump 85 is injected into pump 115, piston 137 moves to the right until piston tip 119 closes oil hole 121. The piston continues its motion to the right compressing the now entrapped oil, and the charge, until its pressure is greater than that in the output tube 135. Valve 113 is then forced open. Piston 137 continues moving to the right thereby expelling the charge out through valve 113 until diaphragm 133 closes against a stop surface 139. At this point, flow through the pump ceases. However, Pittman arm 65 continues its motion to the right thereby compressing a spring 141 in carrier 69. The spring force (hereinafter designated F141) should be sufficiently large that the spring force divided by the cross-sectional area of cylinder 127 is greater than any pressure to be encountered in the output tube 135. This ensures that the diaphragm 133 will always be driven flat against stop 139. It should be noted that diaphragm 133 must be strong enough to avoid rupture when subjected to the spring force. A small disc can be brazed to the diaphragm center to provide added strength.

As was the case for the pump described in connection with FIG. 1, there will be at all times a "dead volume" of liquid present in pump 115, which volume displaces diaphragm 133 away from stop surface 139 when the oil pressure is reduced to atmospheric. As was described in some detail above, on each succeeding stroke, the entire charge delivered from pump 85 to pump 115 will then be reliably delivered by pump 115 to the output. Since metering pump 85 always delivers to the low pressure determined by diaphragm 113, the amount of charge is determined solely by a distance between stops 89 and 109 and may be reliably determined. The overall flow is independent of output pressure since pump 115 subsequently delivers the entire metered charge to the output load for all pressures of interest.

In a pump according to this embodiment of the invention, an additional advantage is that no suction is created by pump 115 which can inadvertently draw a charge up from pump 85. This is achieved by providing that the tensile strength of diaphragm 133 is adequate to maintain the surface flat while piston tip 119 retreats to the left toward oil hole 121. Any vacuum created in the chamber 129 is thus not transmitted across the diaphragm into the pumping chamber of pump 115. In an alternate embodiment, it would also be possible to ensure that this condition is met by including a check valve 124 between the oil reservoir 123 and oil chamber 129 which would allow oil to flow from the reservoir into the chamber during the retreat of piston tip 119. The inclusion of such a check valve reduces the requirements on the tensile strength of diaphragm 133.

Finally, it can be seen that with a pump according to the present invention, it is convenient and inexpensive to achieve gradient elution. It is only necessary that additional metering pumps (e.g., identical in all respects to pump 85) be included so that their outputs feed high pressure pump 115 in parallel with the output of metering pump 85. In FIG. 3 an example of a gradient elution scheme is simply indicated by the presence of a tube 143 which is meant to be the output of a second metering pump. This, in accordance with the principles of this invention, low pressure primary gradient elution which has long been desired in high pressure chromatography is achieved.

I claim:

1. A pumping system comprising:
   first pumping means for metering fluid charges of a desired volume and delivering said metered charges against a predetermined first pressure; and
   second pumping means interconnected with said first pumping means for receiving said metered fluid charges and delivering said fluid charges to a load at a second pressure higher than said first pressure;
   said second pumping means including pressure establishing means for providing said predetermined first pressure against which said first pumping means delivers said metered charges and insuring that no charge is drawn into said second pumping means by action of said second pumping means.

2. A pumping system as in claim 1 wherein said second pumping means comprises:
   a pumping chamber;
   intake means for said pumping chamber;
   exit means for said pumping chamber; and
   a piston for expelling fluid charges in said chamber through said exit means to said load;
   said pressure establishing means including diaphragm means for providing said predetermined first pressure and insuring that no charge is drawn into said pumping chamber by action of said second pumping means.

3. A pumping system as in claim 2 wherein said pressure establishing means further comprises:
   a cavity positioned between said piston and said diaphragm; and
   a reservoir for supplying a reservoir fluid to said cavity to transmit forces from said piston to said diaphragm.

4. A pumping system as in claim 1 wherein said second pumping means includes variable forcing means for exerting a varying pressure on said fluid charges to deliver said fluid charges to a load at said second pressure.

5. A pumping system as in claim 4 wherein said variable forcing means comprises:
   a diaphragm positioned in a cavity of said second pumping means;
   a reservoir for supplying a reservoir fluid to said cavity;
   a piston for transmitting forces to said diaphragm through said reservoir fluid; and
   tension means for exerting a varying pressure on said piston, said varying pressure being transmitted across said diaphragm to deliver said fluid charges to a load at said second pressure.

6. A pumping system as in claim 1 wherein said first pumping means comprises a plurality of independent pumps for metering and delivering an associated plurality of fluids to said second pumping means.

7. A pumping system as in claim 3 wherein said pressure establishing means further comprises:
   valve means interposed between said cavity and said reservoir for allowing reservoir fluid to flow from said reservoir to said cavity during the intake stroke of said pistons to prevent creation of the vacuum in said chamber and insure that no charge is drawn into said second pumping means by action of said second pumping means.

8. A pumping system as in claim 1 wherein said first pumping means comprises:
   a pumping chamber;
   intake means for said pumping chamber;
   exit means for said pumping chamber;
   a pair of stop surfaces positioned in said first pumping means and having an adjustable distance therebetween;
   reciprocating piston means operating between said pair of stop surfaces to draw a desired volume of fluid charge into said pumping chamber and expel said fluid charge from said pumping chamber into said second pumping means, the volume of fluid charge being determined only by the distance between said pair of stop surfaces.

9. A pumping system as in claim 8 wherein said reciprocating piston means comprises:
   an active reciprocating piston;
   return spring means; and
   a passive piston operating in response to said passive piston to expel said fluid charge from said pumping chamber and in response to said return spring means to draw said fluid charge into said pumping chamber.

10. A pumping system as in claim 9 wherein said reciprocating piston means further comprises:
    a reciprocating driver; and
    driver spring means;
    said active reciprocating piston being responsive to said driver spring means to induce positive engagement of said passive piston against one of said stops on the driving stroke of said reciprocating driver.

11. A pumping system as in claim 1 wherein said pressure establishing means comprises:
    a piston stop; and
    spring means for tending to force said piston means against said piston stop on its intake stroke to inhibit the creation of a vacuum in said chamber during said intake stroke, while allowing a desired fluid charge to be introduced into said first pumping means against said first pressure determined by said spring means.

* * * * *